(12) United States Patent
Huang et al.

(10) Patent No.: US 9,512,168 B2
(45) Date of Patent: Dec. 6, 2016

(54) COMPOUND, COMPOSITION AND METHOD FOR TREATING AND/OR AMEOLIORATING KIDNEY DISEASE

(71) Applicant: Trineo Biotechnology Co. LTD., New Taipei (TW)

(72) Inventors: Cheng-Po Huang, Hsinchu (TW); Teng-Hai Chen, Tainan (TW); Kuang Dee Chen, Chiayi (TW); Chun-Tao Su, Taipei (TW)

( * ) Notice: Subject to any disclaimer, the term of this patent is extended or adjusted under 35 U.S.C. 154(b) by 89 days.

(21) Appl. No.: 14/299,671

(22) Filed: Jun. 9, 2014

(65) Prior Publication Data

US 2015/0353595 A1  Dec. 10, 2015

(51) Int. Cl.
*A61K 31/575* (2006.01)
*C07J 9/00* (2006.01)
*A61K 31/00* (2006.01)

(52) U.S. Cl.
CPC ............... *C07J 9/005* (2013.01); *A61K 31/00* (2013.01); *A61K 31/575* (2013.01)

(58) Field of Classification Search
CPC .................................................... A61K 31/575
USPC .................................................. 514/170, 179
See application file for complete search history.

(56) References Cited

FOREIGN PATENT DOCUMENTS

CN         101843828 A  *  9/2010

OTHER PUBLICATIONS

Huang et al., "Ambient molecular imaging of dry fungus surface by electrospray lase desorption ionization mass spectrometry." International Journal of Mass Spectrometry, vol. 325-327, pp. 172-182, 2012.*

Yang et al., "Analysis of triterpenoids in Ganoderma lucicum using liquid chromatography coupled with electrospray ionization mass spectrometry." J. Am. Soc. Mass Spectrom., vol. 18, pp. 927-939, 2007.*

CN101843828 (English translation), 2010.*

* cited by examiner

*Primary Examiner* — Barbara P Badio

(57) ABSTRACT

Disclosed herein are compositions and methods for the treatment or prophylaxis of a subject having or susceptible to a kidney disease. The method includes the step of administering to the subject a compound of formula (I) in a dose of about 1 to 10 mg/Kg to improve the glomerular filtration rate (GFR) of the subject for at least 4 folds as compared to the GFR of the subject before treatment,

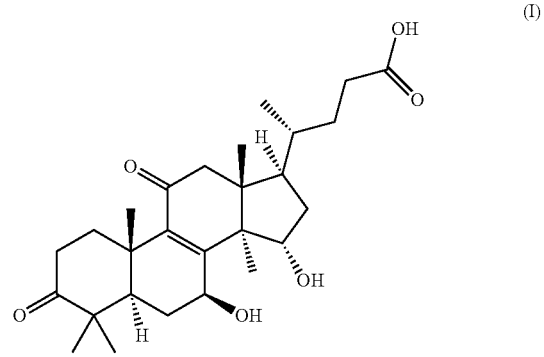

(I)

The method further includes the step of administering to the subject an effective amount of lucidenic acid C (LAC), lucidenic acid N (LAN), lucidenic acid $E_2$ ($LAE_2$), lucidenic acid A (LAA), and lucidenic acid $D_2$ ($LAD_2$).

8 Claims, 6 Drawing Sheets

COMPOUND, COMPOSITION AND METHOD FOR TREATING AND/OR AMEOLIORATING KIDNEY DISEASE

BACKGROUND OF THE INVENTION

1. Field of the Invention

The present disclosure relates to methods and compositions for the treatment or prophylaxis of kidney diseases, including acute kidney injury (AKI) and chronic kidney disease (CKD).

2. Description of Related Art

Acute kidney injury (AKI) or acute renal failure is a syndrome characterized by the rapid loss of the kidney's excretory function and is typically diagnosed by the accumulation of end products of nitrogen metabolism (urea and creatinine) or decreased urine output, or both. It is the clinical manifestation of disorders such as high blood pressure and diabetes that affect the kidney acutely. AKI is common in hospital patients and very common in critically ill patients. Causes of AKI can include, but are not limited to, ischemia/reperfusion, trauma, kidney disease, and kidney transplantation. No specific therapies have emerged that can attenuate AKI or expedite its recovery; thus, most treatment is purely supportive. If patients survive their illness and do not have premorbid chronic kidney disease (CKD), they typically recover to dialysis independence. However, evidence suggests that patients who have had acute kidney injury are at increased risk of subsequent chronic kidney disease.

It is believed that glomerular filtration rate (GFR) is the most relevant metric for determining the extent of AKI and progression of CKD. Reduction in the GFR secondary to kidney injury, either acute or chronic, are accompanied by increases in blood urea nitrogen (BUN) and serum creatinine levels. Thus, if a compound or a composition capable of increasing GFR while reducing or suppressing BUN and serum creatinine levels, such compound or composition would be a potential lead compound or composition for the manufacture of a medicament for the treatment or prophylaxis of kidney disease, including AKI and CKD.

SUMMARY

The present disclosure is based, at least in part, the unexpected discovery that a novel triterpenoid isolated from *Ganoderma lucidum*, and a composition comprising the same, are capable of suppressing BUN and serum creatinine levels, as well as increasing GFR; thus this novel triterpenoid and/or the composition comprising the same may be used for the manufacture of a medicament for the treatment or prophylaxis of kidney disease, including AKI and CKD.

Accordingly, it is the first aspect of the present disclosure to provide a novel triterpenoid isolated from *Ganoderma lucidum* having the structure of formula (I),

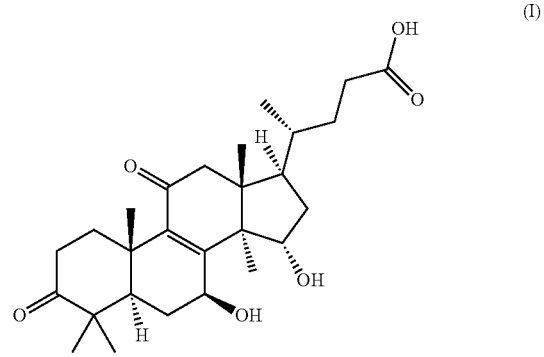 [SMILES: C[C@H](CCC(=O)O)[C@H]1C[C@H](O)[C@@]2(C)C3=C(C(=O)C[C@]12C)[C@@]1(C)CCC(=O)C(C)(C)[C@@H]1C[C@@H]3O]

The second aspect of this disclosure is to provide a pharmaceutical composition for the treatment or prophylaxis of a kidney disease. The pharmaceutical composition includes a therapeutically effective amount of the compound of formula (I); and at least another triterpenoid that is any of lucidenic acid C (LAC), lucidenic acid N (LAN), lucidenic acid $E_2$ ($LAE_2$), lucidenic acid A (LAA), lucidenic acid B (LAB), or lucidenic acid $D_2$ ($LAD_2$); and a pharmaceutically acceptable excipient.

According to one preferred embodiment, the pharmaceutical composition comprises the compound of formula (I), LAC, LAA, $LAD_2$, LAB, LAN, and $LAE_2$; and a pharmaceutically acceptable excipient; wherein the triterpenoid compound of formula (I) and LAC are present in about 5-15% by weight of the total triterpenoid in the pharmaceutical composition, LAB and LAN are respectively present in about 5-12% by weight of the total triterpenoid in the pharmaceutical composition, LAA and $LAD_2$ are respectively present in about 15-30% by weight of the total triterpenoid in the pharmaceutical composition, and $LAE_2$ is present in about 8-15% by weight of the total triterpenoid in the pharmaceutical composition.

The kidney disease treatable or preventable by the pharmaceutical composition of this disclosure is acute kidney injury (AKI) or chronic kidney disease (CKD). In one example, the kidney disease is AKI, particularly, acute kidney inflammation. In another example, the kidney disease is CKD, such as chronic kidney inflammation.

The novel combination of triterpenoids of this disclosure, specifically the combination of the compound of formula (I), LAC, LAA, $LAD_2$, LAB, LAN, and $LAE_2$, is present at a level of about 0.1% to 99% by weight, based on the total weight of the pharmaceutical composition. In some embodiments, the combination of the triterpenoids of this disclosure is present at a level of at least 1% by weight, based on the total weight of the pharmaceutical composition. In certain embodiments, the combination of the triterpenoids of this disclosure is present at a level of at least 5% by weight, based on the total weight of the pharmaceutical composition. In still other embodiments, the combination of the triterpenoids of this disclosure is present at a level of at least 10% by weight, based on the total weight of the pharmaceutical composition. In still yet other embodiments, the combination of the triterpenoids is present at a level of at least 25% by weight, based on the total weight of the pharmaceutical composition.

It is therefore the third aspect of this disclosure to provide a method of treating a kidney disease in a subject. The method includes the step of administering to the subject a therapeutically effective amount of the compound of formula (I) or a composition comprising the same to improve or ameliorate the symptoms of the kidney disease.

According to one preferred example, the method includes the step of administering the compound of formula (I) in a dose of about 1 to 10 mg/Kg to improve the glomerular filtration rate (GFR) of the subject for at least 4 folds as compared to the GFR of the subject before treatment.

According to another example, the method includes the step of administering the composition of the present invention to the subject to improve or ameliorate the symptoms of the kidney disease. Preferably, the composition comprises the compound of formula (I), LAC, LAA, $LAD_2$, LAB, LAN, and $LAE_2$, and a pharmaceutically acceptable carrier, wherein the amount of the compound of formula (I), LAC, LAA, $LAD_2$, LAB, LAN, and $LAE_2$ are respectively about 10%, 10%, 10%, 8.5%, 15%, 25% and 25% by weight of the total triterpenoid in the pharmaceutical composition. Kidney diseases that may be treated or prevented from occurring include, but is not limited to, AKI and CKD. In one example, the kidney disease is AKI, particularly, acute kidney inflammation. In another example, the kidney disease is CKD, such as chronic kidney inflammation. The subject may be a mammal, preferably a human.

The details of one or more embodiments of this disclosure are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The accompanying drawings, which are incorporated in and constitute a part of the specification, illustrate various example systems, methods and other exemplified embodiments of various aspects of the invention. The present description will be better understood from the following detailed description read in light of the accompanying drawings, where.

DETAILED DESCRIPTION OF PREFERRED EMBODIMENTS

Figure 1:
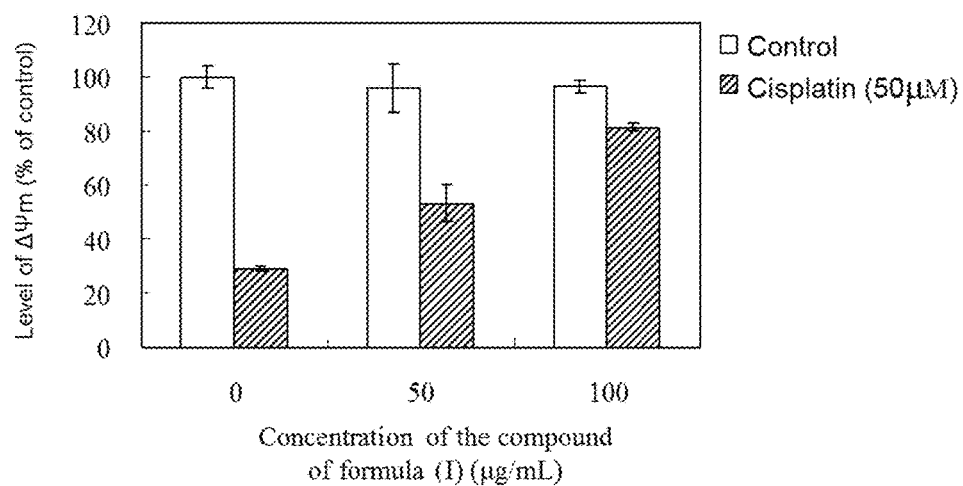
FIG. 1A is illustrates the protective effect of the compound of formula (I) on cisplatin induced kidney cell apoptosis in accordance with one embodiment of the present disclosure.
FIG. 1B illustrates the protective effect of the composition YKII-10 of example 1.2 on cisplatin induced kidney cell apoptosis in accordance with one embodiment of the present disclosure.
Figure 1:
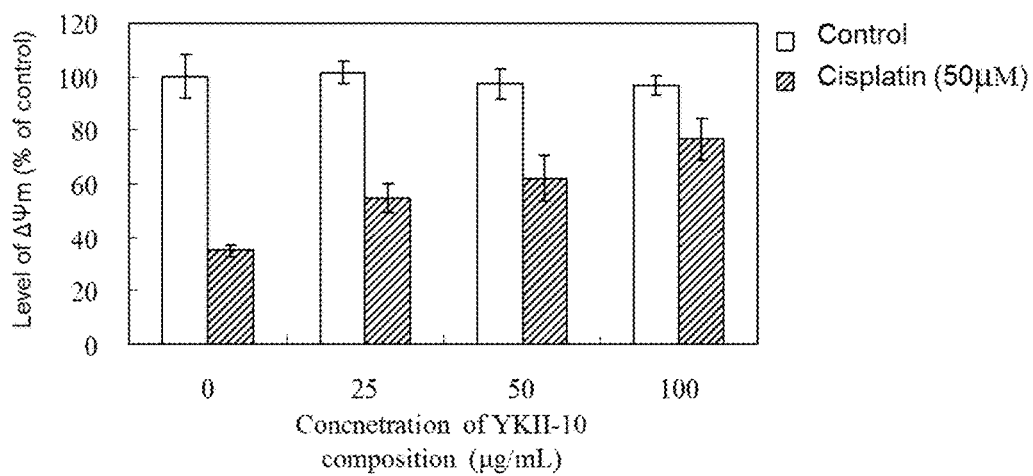

The detailed description provided below in connection with the appended drawings is intended as a description of the present disclosure and is not intended to represent the only forms in which the present disclosure may be constructed or utilized.

In the context of this disclosure, a number of terms shall be used.

The terms "treatment" and "treating" are used herein to include preventative (e.g., prophylactic), curative, or palliative treatment that results in a desired pharmaceutical and/or physiological effect. Preferably, the effect is therapeutic in terms of partially or completely curing or preventing the apoptosis of kidney cells. Also, the term "treating" as used herein refers to application or administration of the compound or the composition of the present disclosure to a subject, who has a medical condition, a symptom of the condition, a disease or disorder secondary to the condition, or a predisposition toward the condition, with the purpose to partially or completely alleviate, ameliorate, relieve, delay onset of, inhibit progression of, reduce severity of, and/or reduce incidence of one or more symptoms or features of a particular disease, disorder, and/or condition. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. As used herein, the symptom, disease, disorder or condition may be acute kidney injury (AKI) or chronic kidney disease (CKD). Treatment is generally "effective" if one or more symptoms or clinical markers are reduced as that term is defined herein.

The term "prophylaxis" as used herein means prevention against a future event. In the context of prophylaxis against kidney cells apoptosis that may potentially occur as a consequence of kidney cells being exposed under a toxic compound or a medicament, the prophylactic administration can occur before, contemporaneous with, and/or after the subject being exposed under the toxic compound or medicament. According to some embodiments of the present disclosure, the compound of formula (I) or a composition comprising the same is prophylactically administered to the subject before the subject is exposed to a toxic compound such as cisplatin, lipopolysaccharide (LPS) or aristolochic acid (AAI), that results in kidney inflammation and/or damage.

The terms "compounds," "compositions," "agent" and "medicament" are used interchangeably herein to refer to a compound or a composition of which, when administered to a subject such as a human or an animal induces a desired pharmacological and/or physiological effect by local and/or systemic action.

The terms "administered," "administering" and "administration" are used interchangeably herein to refer means either directly administering a compound or a composition of the present invention, or administering a prodrug, derivative or analog which will form an equivalent amount of the active compound of formula (I) within the body.

The term "subject" or "patient" refers to an animal including the human species that is treatable with the compositions and/or methods of the present invention. The term "subject" or "patient" intended to refer to both the male and female gender unless one gender is specifically indicated. Accordingly, the term "subject" or "patient" includes, but is not limited to, human, non-human primate such as any mammal, dog, cat, horse, sheep, pig, cow and etc., preferably a human, which may benefit from treatment by the compound of this disclosure. The terms "subject" and "patient" are used interchangeably in the present disclosure.

The term "an effective amount" as used herein refers to an amount effective, at dosages, and for periods of time necessary, to achieve the desired therapeutically result with respect to the treatment of a kidney disease. The effective amount of the compound of formula (I), its salt, ester or solvate may be ranged from about 0.1 mg/Kg/day to about 100 mg/Kg/day; preferably from about 1 mg/Kg/day to about 50 mg/Kg/day; more preferably from about 5 mg/Kg/day to about 10 mg/Kg/day. The effective amount may vary depends on the route of administration, and/or other the combinational use of other medicaments.

Throughout the specification, unless otherwise indicated to the contrary, the term "triterpenoid" herein means to encompass the triterpenoid, as well as its pharmaceutically acceptable salts, esters or solvates. For example, the triterpenoid compound of formula (I) of the present disclosure is meant to encompass the triterpenoid compound of formula (I), and its pharmaceutically acceptable salts, esters or solvates. The term "salt" refers herein as a salt which is formed by the interaction of a base including organic or inorganic types of bases, including bases formed from a metal of the IA or IIA group, ammonium and/or $N(alkyl)_4^+$ with an acid (such as the compound of formula (I) in this disclosure). The term "ester" herein refers to an ester of the compound of formula (I), in which the ester bond may be formed between the acid group of the compound of formula (I) and an alcohol, such as straight or branched $C_{1-6}$ alcohol; or between the hydroxyl group of the compound of formula (I) and an organic acid, such as R—COOH, wherein R is a straight or branched $C_{1-6}$ alkyl. The term "solvate" herein refers to a complex formed by the interaction of a compound (such as the compound of formula (I) in this disclosure) with surrounding solvent molecules, such as water, ethanol and etc.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The present disclosure is based, at least in part, unexpected discovery that a novel triterpenoid isolated from the fruit bodies or mycelia of *Ganoderma lucidum* may suppress or inhibit apoptosis of kidney cells, and thereby results in a decrease in BUN and serum creatinine levels, and an increase in glomerular filtration rate (GFR). The results suggest that the novel triterpenoid of the present disclosure is useful as a therapeutic medicament for the treatment or prophylaxis of kidney disease, such as AKI and CKD.

Accordingly, one objective of this disclosure is to provide a novel triterpenoid compound of formula (I),

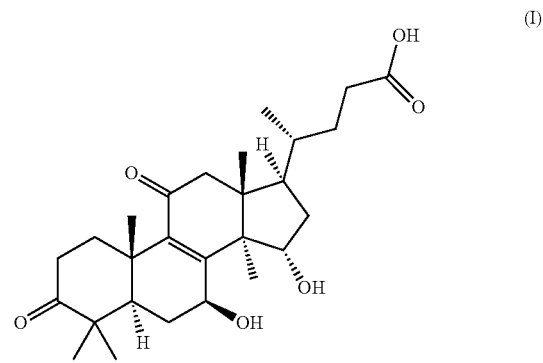 [SMILES: C[C@H](CCC(=O)O)[C@H]1C[C@H](O)[C@@]2(C)C3=C(C(=O)C[C@]12C)[C@@]1(C)CCC(=O)C(C)(C)[C@@H]1C[C@@H]3O]

According to embodiments of the present disclosure, the compound of formula (I) is effective in suppressing cisplatin or aristolochic acid (AAI) induced kidney inflammation and/or damage manifesting in the increase in blood urea nitrogen and serum creatinine levels; as well as in ameliorating cisplatin or AAI induced kidney cell apoptosis; thus the compound of formula (I) may be used as a lead compound for the manufacture of a medicament for the treatment or prophylaxis of a kidney disease, such as AKI or CKD.

Inventors of the present disclosure also identify a novel combination of triterpenoids, in which each triterpenoid may be isolated from the fruit bodies or mycelia of *Ganoderma lucidum*. This novel combination of triterpenoids is also effective in suppressing cisplatin induced kidney cell apoptosis, ameliorating LPS or AAI induced kidney inflammation and/or damage; thus may also be used for the manufacture of a medicament for the treatment or prophylaxis of a kidney disease, such as AKI or CKD.

It is therefore a further objective of this disclosure to provide a pharmaceutical composition, which comprises the novel combination of triterpenoids described above, for the treatment or prophylaxis of a kidney disease. The pharmaceutical composition includes a therapeutically effective amount of the compound of formula (I), LAC, LAN, $LAE_2$, LAA, LAB, and $LAD_2$; and a pharmaceutically acceptable carrier.

According to some embodiments, the amounts of the compound of formula (I) and LAC are respectively about 5-15% by weight of the total triterpenoid in the pharmaceutical composition, such as 5, 5.5, 6, 6.5, 7, 7.5, 8, 8.5, 9, 9.5, 10, 10.5, 11, 11.5, 12, 12.5, 13, 13.5, 14, 14.5 and 15% by weight of the total triterpenoid in the pharmaceutical composition. In a preferred embodiment, the amounts of the compound of formula (I) and LAC are respectively about 10% by weight of the total triterpenoid in the pharmaceutical composition.

In still some other embodiments, the amounts of LAA and $LAD_2$ are respectively about 15-30% by weight of the total triterpenoid in the pharmaceutical composition, such as 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5 and 30% by weight of the total triterpenoid in the pharmaceutical composition. In a preferred embodiment, the amount of LAA and $LAD_2$ are respectively about 25% by weight of the total triterpenoid in the pharmaceutical composition.

In other embodiments, the amount of $LAE_2$ is about 8-15% by weight of the total triterpenoid in the pharmaceutical composition, such as 8, 8.5, 9, 9.5, 10, 10.5, 11, 11.5, 12, 12.5, 13, 13.5, 14, 14.5 and 15% by weight of the total triterpenoid in the pharmaceutical composition. In a preferred embodiment, the amount of $LAE_2$ is about 12% by weight of the total triterpenoid in the pharmaceutical composition.

In still some other embodiments, the amounts of LAN and LAB are respectively about 5-12% by weight of the total triterpenoid in the pharmaceutical composition, such as 5, 5.5, 6, 6.5, 7, 7.5, 8, 8.5, 9, 9.5, 10, 10.5, 11, 11.5, and 12% by weight of the total triterpenoid in the pharmaceutical composition. In a preferred embodiment, the amounts of LAN and LAB are respectively about 8.5% by weight of the total triterpenoid in the pharmaceutical composition.

In one preferred embodiment, the pharmaceutical composition comprises the compound of formula (I), LAC, LAN, $LAE_2$, LAA, LAB, and $LAD_2$; and a pharmaceutically acceptable carrier; and wherein the amounts of the compound of formula (I), LAC, LAN, $LAE_2$, LAA, and $LAD_2$ are respectively about 10%, 10%, 8.5%, 15%, 25% and 25% by weight of the total triterpenoid in the pharmaceutical composition.

The respective triterpenoids in the pharmaceutical composition of the present disclosure may be purified from the fruit bodies or mycelia of *Ganoderma lucidum* by methods well known in the art or by similar methods set forth in example 1 of the present disclosure. Whether the raw material used for isolating triterpenoids is the fruit bodies or the mycelia, such method in general involves extracting the plant with a solvent, preferably an alcoholic solution, at a temperature above room temperature; followed by subjecting the extract with column chromatography, which includes but is not limited to, high performance liquid chromatography (HPLC), reverse phase liquid chromatography and etc.; and concentrating and drying, until a dried powder is obtained.

Generally, the triterpenoids of the present disclosure, specifically the combination of the compound of formula (I), LAC, LAN, $LAE_2$, LAA, LAB, and $LAD_2$, is present at a level of about 0.1% to 99% by weight, based on the total weight of the pharmaceutical composition. In some embodiments, the combination of the triterpenoids of the present disclosure is present at a level of at least 1% by weight, based on the total weight of the pharmaceutical composition. In certain embodiments, the combination of the triterpenoids of the present disclosure is present at a level of at least 5% by weight, based on the total weight of the pharmaceutical composition. In still other embodiments, the combination of the triterpenoids of the present disclosure is present at a level of at least 10% by weight, based on the total weight of the pharmaceutical composition. In still yet other embodiments, the combination of the triterpenoids is present at a level of at least 25% by weight, based on the total weight of the pharmaceutical composition.

Kidney disease that may be treated by the compound of formula (I) or by the pharmaceutical composition of this disclosure include, but are not limited to, acute kidney injury and chronic kidney disease. In one example, the compound of formula (I) is used to treat AKI, such as cisplatin or AAI-induced kidney inflammation. In another example, the pharmaceutical composition of this disclosure, or the pharmaceutical composition comprising the compound of formula (I), is employed to treat AKI.

The medicament or said pharmaceutical composition is prepared in accordance with acceptable pharmaceutical procedures, such as described in Remington's Pharmaceutical Sciences, $17^{th}$ edition, ed. Alfonoso R. Gennaro, Mack Publishing Company, Easton, Pa. (1985). Pharmaceutically acceptable excipients are those that are compatible with other ingredients in the formulation and biologically acceptable.

The pharmaceutical composition of the present disclosure may be administered by any suitable route, for example, orally in capsules, suspensions or tablets or by parenteral administration. Parenteral administration can include, for example, systemic administration such as intramuscular, intravenous, subcutaneous, or intraperitoneal injection. The pharmaceutical composition can also be administered transdermally either topically or by inhalation (e.g., intrabronchial, intranasal, oral inhalation or intranasal drops), or rectally, alone or in combination with conventional pharmaceutically acceptable excipients. In preferred embodiments, the pharmaceutical composition of the present disclosure are administered orally (e.g., dietary) to the subject.

For oral administration, the pharmaceutical composition of the present disclosure may be formulated into tablets containing various excipients such as microcrystalline cellulose, sodium citrate, calcium carbonate, dicalcium phosphate, and glycine; along with various disintegrants such as starch, alginic acid and certain silicates; together with granulation binders like polyvinylpyrrolidone, sucrose, gelatin and acacia. Additionally, lubricating agents such as magnesium stearate, sodium lauryl sulfate and talc may be added. Solid composition may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and if so desired, emulsifying and/or suspending agents as well, together with diluents such as water, ethanol, propylene glycol, glycerin and a combination thereof.

For parenteral administration, the novel combination of triterpenoids of the present disclosure may be formulated into liquid pharmaceutical compositions, which are sterile solutions, or suspensions that can be administered by, for example, intravenous, intramuscular, subcutaneous, or intraperitoneal injection. Suitable diluents or solvent for manufacturing sterile injectable solution or suspension include, but are not limited to, 1,3-butanediol, mannitol, water, Ringer's solution, and isotonic sodium chloride solution. Fatty acids, such as oleic acid and its glyceride derivatives are also useful for preparing injectables, as are natural pharmaceutically-acceptable oils, such as olive oil or castor oil. These oil solutions or suspensions may also contain alcohol diluent or carboxymethyl cellulose or similar dispersing agents. Other commonly used surfactants such as Tweens or Spans or other similar emulsifying agents or bioavailability enhancers that are commonly used in manufacturing pharmaceutically acceptable dosage forms can also be used for the purpose of formulation.

For transmucosal administration, the medicament or said pharmaceutical compositions of the present disclosure may also be formulated in a variety of dosage forms for mucosal application, such as buccal and/or sublingual drug dosage units for drug delivery through oral mucosal membranes. A wide variety of biodegradable polymeric excipients may be used that are pharmaceutically acceptable, provide both a suitable degree of adhesion and the desired drug release profile, and are compatible with the active agents to be administered and any other components that may be present in the buccal and/or sublingual drug dosage units. Generally, the polymeric excipient comprises hydrophilic polymers that adhere to the wet surface of the oral mucosa. Examples of polymeric excipients include, but are not limited to, acrylic acid polymers and copolymers; hydrolyzed polyvinylalcohol; polyethylene oxides; polyacrylates; vinyl polymers and copolymers; polyvinylpyrrolidone; dextran; guar gum; pectins; starches; and cellulosic polymers.

It will be appreciated that the dosage of the pharmaceutical composition of the present disclosure will vary from patient to patient not only for the particular route of administration, and the ability of the composition to elicit a desired response in the patient, but also factors such as disease state or severity of the condition to be alleviated, age, sex, weight of the patient, the state of being of the patient, and the severity of the pathological condition being treated, concurrent medication or special diets then being followed by the patient, and other factors which those skilled in the art will recognize, with the appropriate dosage ultimately being at the discretion of the attendant physician. Dosage regimens may be adjusted to provide the improved therapeutic response. A therapeutically effective amount is also one in which any toxic or detrimental effects of the composition are outweighed by the therapeutically beneficial effects. Preferably, the compositions of the present disclosure are administered at a dosage and for a time such that the number and/or severity of the symptoms are decreased.

The pharmaceutical composition of the present disclosure may be administered to a subject in a dose from about 0.1 mg to about 100 mg per kilogram of body weight per day, such as 0.1, 0.5, 1, 2, 5, 7, 9, 10, 12, 15, 17, 19, 20, 22, 25, 27, 29, 30, 32, 35, 37, 39, 40, 42, 45, 47, 49, 50, 52, 55, 57, 59, 60, 62, 65, 67, 69, 70, 72, 75, 77, 79, 80, 82, 85, 87, 89, 90, 92, 95, 97, 99 and 100 mg/Kg/day; preferably from about 1 to 50 mg per kilogram of body weight per day, such as 1, 2, 5, 7, 9, 10, 12, 15, 17, 19, 20, 22, 25, 27, 29, 30, 32, 35, 37, 39, 40, 42, 45, 47, 49, and 50 mg/Kg/day; more preferably from about 5 to 10 mg per kilogram of body weight per day, such as 5, 7, 8, 9, and 10 mg/Kg/day. The dose may be administered once a day or be at least two, three, four, or five times a day.

The present disclosure also provides a method of treating a kidney disease in a subject. The method includes the step of administering to the subject an effective amount of the compound of formula (I) or the composition of the present disclosure to the subject to improve or ameliorate the symptoms of the kidney disease, such as protecting the kidney cells from apoptosis or improving glomerular filtration rate (GFR).

According to one example, the method includes the step of administering the compound of formula (I) to the subject in a dose of about 1 to 10 mg/Kg to improve GFR of the subject for at least 4 folds as compared to the GFR of the subject before treatment. The method further includes steps of administering to the subject, about 1 to 10 mg/Kg LAC, respectively about 2.5 to 25 mg/Kg of LAA and $LAD_2$, about 1.5 to 15 mg/Kg $LAE_2$, and respectively about 0.85 to 8.5 mg/Kg LAN and LAB.

According to another example, the method includes the step of administering to the subject a therapeutically amount of the composition of the present disclosure to improve GFR of the subject for at least 4 folds, as compared to the GFR of the subject before treatment. Preferably, the composition comprises the compound of formula (I), LAC, LAA, $LAD_2$, LAB, LAN, and $LAE_2$, and a pharmaceutically acceptable carrier, wherein the amount of the compound of formula (I), LAC, LAA, $LAD_2$, LAB, LAN, and $LAE_2$ are respectively about 10%, 10%, 10%, 8.5%, 15%, 25% and 25% by weight of the total triterpenoid in the pharmaceutical composition. The compound of formula (I) or the composition is administered to a mammal, preferably human, by any route that may effectively transports the active ingredient(s) of the composition to the appropriate or desired site of action, such as oral, nasal, pulmonary, transdermal, such as passive or iontophoretic delivery, or parenteral, e.g., rectal, depot, subcutaneous, intravenous, intramuscular, intranasal, ophthalmic solution or an ointment.

The present invention will now be described more specifically with reference to the following embodiments, which are provided for the purpose of demonstration rather than limitation.

EXAMPLES

Materials and Methods
Cell Culture
Madin-Darby canine kidney (MDCK) cells ($1.5 \times 10^5$ cells/mL) were cultured and maintained in Dulbecco's modified Eagle medium (DMEM) supplemented with 10% fetal bovine serum (FBS), 100 units/mL penicillin, 100 ng/mL streptomycin, 2 mM L-glutamine, non-essential amino acids and sodium pyruvate, and maintained in 5% $CO_2$ at 37° C. until reached 80% confluence, then were subject to cell passages.

Animals
Blb/c mice were kept in pathogen-free environment under 12:12 light-dark cycle with food (laboratory rodent diet 5001 purchased from PMI Nutrition International Inc. MO, USA) and water (i.e., distilled water) provided ad libitum, ambient temperature and relative humidity were respectively set at 22±3° C. and 50±20%. All procedures involving animal studies of the present disclose e comply with the "Guideline for the Care and Use of Laboratory Animals" issued by The Chinese-Taipei Society of Laboratory Animal Sciences.

Example 1

Isolation of the Compound of Formula (I) and the Preparation of the Composition of the Present Disclosure 1.1 Identification and Characterization of the Compound of Formula (I)

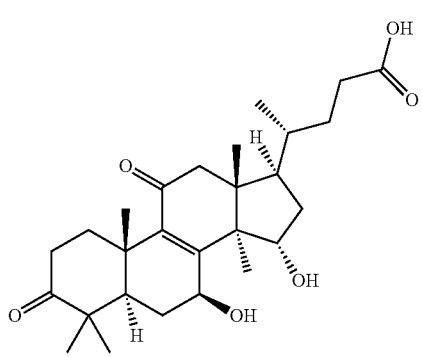

The fruiting bodies of Ganoderma lucidum (50 g) were grounded to powders, and extracted with ethanol in a ratio of G. lucidum (weight) to ethanol (volume)=1:24 at 37° C. for a day, the extract was then subject to concentration. The extraction and concentration steps were repeated several times, and the respective extracts were filtered, combined and dried with a yield crude extract of about 10% (i.e., 5 g of crude extract). The resultant crude extract of G. lucidum was then vacuumed dried at about 40° C. to remove any residual solvent.

5 g of the crude extract of G. lucidum prepared above was subsequently subject to extraction with ethyl acetate (EA), the EA extract was then concentrated, and vacuumed dried at about 40° C. to remove residual solvent. The yield of the EA extract of G. lucidum was about 40% (or 2.0 g).

The EA extract of G. lucidum was dissolved in ethanol and subjected to semi-preparative high pressure liquid chromatography, in which the column was eluted with cyanomethane and 2% acetic acid, and the compound of formula (I) was identified therein with a yield of about 0.4% (8 mg).

The $^{13}C$ and $^1H$ NMR spectra, as well as heteronuclear multiple bond correlation (HMBC) spectra of the compound of formula (I) are summarized in Table 1.

TABLE 1

The spectra data of the compound of formula (I)

| C No. | $d_C$ | $d_H$ | HMBC (H to C) |
|---|---|---|---|
| 1 | 35.5 | 1.46 (a, m), 2.85 (b, ddd, 6.6, 7.0, 13.6) | 2, 3, 5, 10, 19 |
| 2 | 34.3 | 2.49 (2H, dd, 7.0, 8.4). | 1, 3, 4, 10 |
| 3 | 217.0 | | |
| 4 | 46.8 | | |
| 5 | 48.8 | 1.68 (m) | 1, 4, 10, 19, 26, 27 |
| 6 | 28.9 | 2.04 (a, dd, 3.6, 11.3), 1.66 (b) | 4, 8, 10 |
| 7 | 68.9 | 4.63 (dd, 6.9, 9.5) | 8, 9, 25 |
| 8 | 159.1 | | |
| 9 | 140.4 | | |
| 10 | 38.0 | | |
| 11 | 199.8 | | |

TABLE 1-continued

The spectra data of the compound of formula (I)

| C No. | $d_C$ | $d_H$ | HMBC (H to C) |
|---|---|---|---|
| 12 | 51.8 | 2.75 (a, d, 15.9), 2.52, (b, d, 15.9) | 9, 11, 13, 14, 18 |
| 13 | 46.7 | | |
| 14 | 53.9 | | |
| 15 | 72.6 | 4.80 (dd, 6.9, 9.6) | 8, 14, 25 |
| 16 | 36.4 | 1.84 (a, m), 1.88 (b, m) | 25 |
| 17 | 48.5 | 1.78 (m) | 21 |
| 18 | 17.2 | 0.96 (s) | 12, 13, 14, 17 |
| 19 | 19.4 | 1.29 (s) | 1, 5, 9, 10, 27 |
| 20 | 35.7 | 1.47 (m) | 21 |
| 21 | 18.1 | 0.89 (d, 6.5) | 17, 20, 22 |
| 22 | 30.9 | 1.81 (m) | 21 |
| 23 | 30.9 | 2.41 (m), 2.31 (ddd, 8.0, 8.1, 16.0) | 21 |
| 24 | 177.9 | | |
| 25 | 19.4 | 1.26 (s) | 8, 13, 14, 15 |
| 26 | 27.3 | 1.12 (s) | 3, 4, 5, 27 |
| 27 | 20.7 | 1.11 (s) | 3, 4, 5, 26 |

The molecular of formula (I) was determined as $C_{24}H_{40}O_6$ from its HRMS m/z=460.2834 as well as from the $^{13}C$ and $^1H$ NMR.

The MS of formula (I) showed fragmented ions at m/z (rel. int.): 460 [M+] (53.56), 442 (22.56), 339 (16.46), 322 (100), 304 (46.41); and its IR spectra showed absorption bands at 3445, 1736, 1707, 1661 $cm^{-1}$; and UV spectra showed maximum absorption (MeOH, $1_{max}$) at 252 nm; with a melting point between 124-126° C.

1.2 Preparation of the Pharmaceutical Composition YKII-10 Comprising the Compound of Formula (I)

The pharmaceutical composition of the present disclosure (or YKII-10 composition) for treating kidney disease is prepared by mixing the compound of formula (I) of example 1.1 with other triterpenoids in accordance with the formulation listed in Table 2. The triterpenoids of Table 2 may be obtained by extracting the fruting bodies and/or mycelia of Ganoderma spp. with any solvent(s), followed by separation with suitable chromatography.

TABLE 2

The YKII-10 formulation

| Name of Compound | % of Total Triterpenoids |
|---|---|
| LAA | 24.2% |
| LAB | 8.3% |
| LAC | 10.7% |
| $LAD_2$ | 25.9% |
| $LAE_2$ | 12.3% |
| LAN | 8.6% |
| The compound of formula (I) | 10% |
| Total Triterpenoids | 100% |

Example 2

Both the Compound of Formula (I) and the YKII-10 Composition of Example 1.2 are Effective in Ameliorating or Improving Cisplatin Induced Kidney Inflammation In the present example, in vitro kidney cell apoptosis and in vivo kidney inflammation were respectively used as indicators for assessing the protective effect rendered by the compound of formula (I) and the YKII-10 composition of example 1.2.

2.1 Cisplatin Induced In Vitro Kidney Cell Apoptosis

MDCK cells were cultured in according to procedures described in the "Materials and Methods" section. To start the experiment, MDCK cells were first incubated with 50 μM cisplatin for 4 hrs, then various concentrations of the compound of formula (I) (50 μm/mL or 100 μg/mL) or the YKII-10 composition of example 1.2 (25 to 100 μg/mL) were given to cisplatin-treated cells and further incubated for another 24 hrs. Mitochondria membrane potentials were then measured by staining the live cells with fluorescent dyes (e.g., 50 nM DiOC6), in which 50 nM DiOC6 were added to cells and incubated at 37° C. for 30 min. The cells were then washed twice with phosphate buffer solution before subjecting to microscopy analysis using the inverted fluorescent microscope. Since only live cells are capable of taking up the DiOC6 dye, hence the test is useful for evaluating any effect of a candidate compound (e.g., the compound of formula (I) or the YKII-10 composition of example 1.2) on the progression of apotosis. Results are illustrated in FIGS. 1A and 1B.

As the bar graph of FIG. 1A illustrated, the compound of formula (I) (50 μg/mL or 100 μg/mL) is capable of reversing cisplatin-induced apoptosis of MDCK cell, with about 80% recovery on the membrane potential at the dose of 100 μg/mL. Similar results were also observed when the YKII-10 composition of example 1.2 was employed, in which the membrane potential of MDCK cells increased in a dose dependent manner from 25 to 100 μg/mL. Taken together, the results from this example indicate that both the compound of formula (I) and the YKII-10 composition comprising the compound of formula (I) are both effective in reversing cisplatin induced apoptosis, thus the compound of formula (I) and the composition of example 1.2 may be used to treat or ameliorate kidney disease (e.g., kidney inflammation).

2.2 Cisplatin Induced In Vivo Kidney Inflammation

Figure 2:
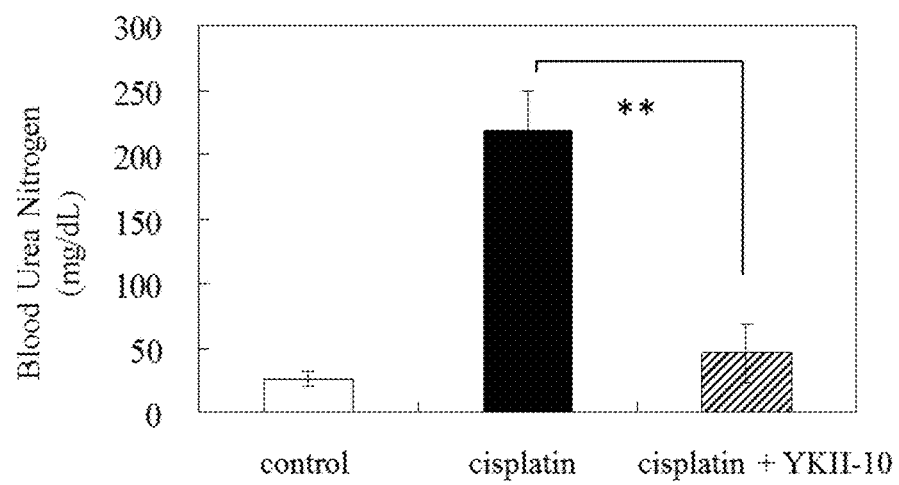
FIG. 2A illustrates the inhibitory effect of the composition YKII-10 of example 1.2 on cisplatin induced increase in blood urea nitrogen in accordance with one embodiment of the present disclosure.
FIG. 2B illustrates the inhibitory effect of the composition YKII-10 of example 1.2 on cisplatin induced increase in serum creatinine level in accordance with one embodiment of the present disclosure.
Figure 2:
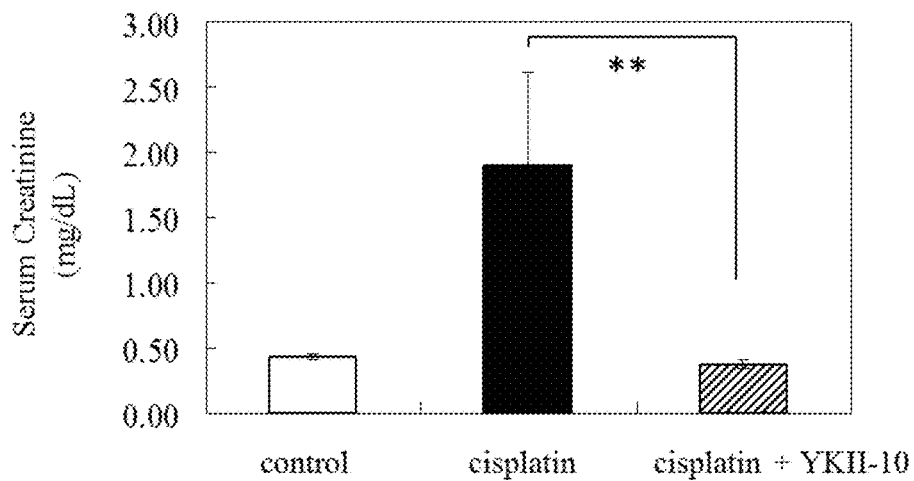

On the first day of this experiment, Blb/c mice (6 weeks old) were randomly assigned to two groups, with the mice in the test group being orally given the YKII-10 composition of example 1.2 (10 mL/Kg) for 5 days, and the mice in the control group were given just the distilled water. All animals were injected intraperitonealy with cisplatin (15 mg/Kg) on the second day, and blood samples were collected on the fifth day, then analyzed for blood urine nitrogen (BUN), and creatinine (CRE), which were used as indicators for assessing the kidney function. Results are illustrated in FIG. 2.

As depicted in FIG. 2A and FIG. 2B, both the levels of BUN and CRE increased after the injection of cisplatin, and this cisplatin induced increases in BUN and CRE were both suppressed in the presence of the YKII-10 composition of example 1.2, in which the compound of formula (I) is included. Thus, the data supports the proposition that the composition comprising the compound of formula (I) of the present invention may be used for the treatment or prophylaxis of kidney disease.

Example 3

Both the Compound of Formula (I) and the YKII-10 Composition of Example 1.2 are Effective in Ameliorating or Improving Lipopolysaccharide Induced Kidney Inflammation In this example, to evaluate the therapeutic or prophylactic function of the composition of example 1.2, animals were first injected intraperitoneally with lipopolysaccharide (LPS) to induce in vivo kidney inflammation before being subject to the treatment of the composition of example 1.2.

Blb/c mice (6 weeks old) were randomly assigned to two groups, and injected intraperitoneally with lipopolysaccharide (LPS, 2.5 mg/Kg/day) for 5 consecutive days so as to induce kidney inflammation. In the mean time, mice in the test group were orally fed with either the compound of formula (I) (at a dosage of 100 mg/Kg) or the YKII-10 composition of example 1.2 (at a dosage of 250 mg/Kg), while the animals in the control group were given just the water. Urine samples were respectively collected on the fifth and the tenth day after the experiment started, and analyzed for the level of urine protein therein. The results are depicted in FIG. 3.

Figure 3:
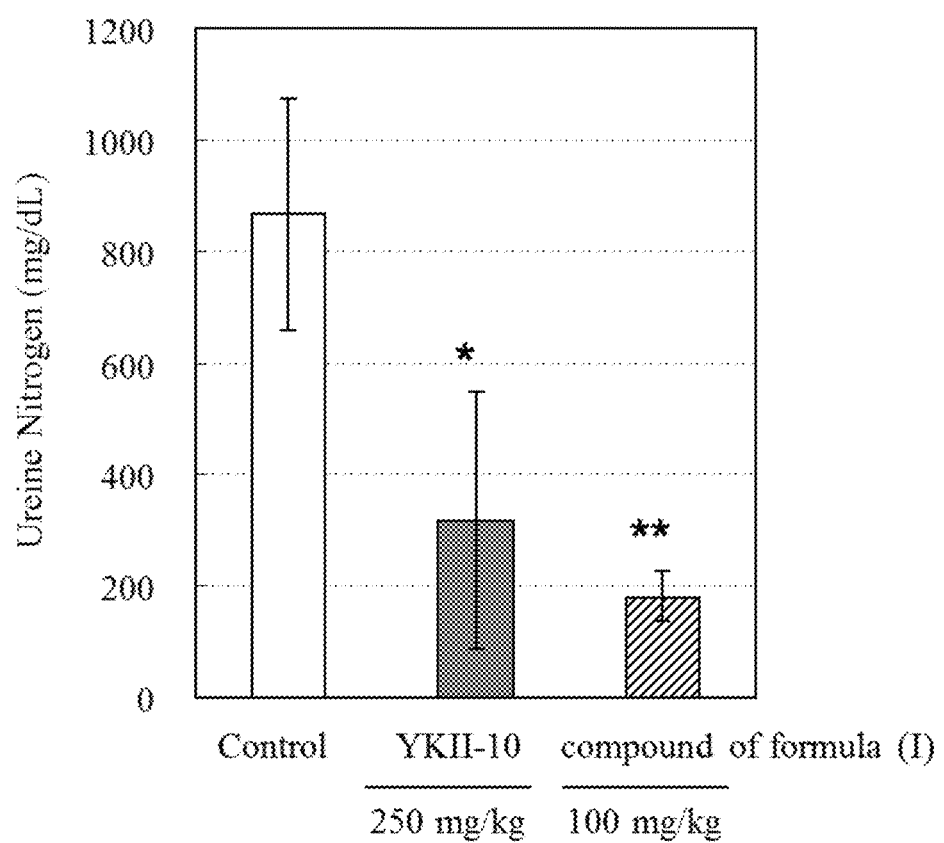
FIG. 3 illustrates the respective inhibitory effects of the compound of formula (I) and the composition YKII-10 of example 1.2 on lipopolysaccharide (LPS) induced increase in urea protein in accordance with one embodiment of the present disclosure.

As depicted in FIG. 3, both the compound of formula (I) and the YKII-10 composition (i.e., the composition of example 1.2) are effective in reducing the urine protein level in the test animals, which support the hypothesis that the compound of formula (I) or the composition comprising the compound of formula (I) may be used for the treatment or prophylaxis of kidney disease.

Example 4

YKII-10 Composition of Example 1.2 is Effective in Ameliorating or Improving In Vivo Aristolochic Acid (AAI) Induced Acute Kidney Injury (AKI)

4.1 AAI Induced In Vivo Acute Kidney Injury

Blb/c mice (6 weeks old) were randomly assigned to two groups, and orally fed with AAI (2.5 mg/Kg/day) for 5 consecutive days, so as to induce AKI. Mice in the test group were orally fed with the YKII-10 composition of example 1.2 (at a dosage of 300 mg/Kg) for 12 consecutive days, while the animals in the control group were given just the water. Blood samples were respectively collected on the 12th day after the experiment started, and analyzed for the level of BUN and CRE. The results are depicted in FIGS. 4A and 4B.

Figure 4:
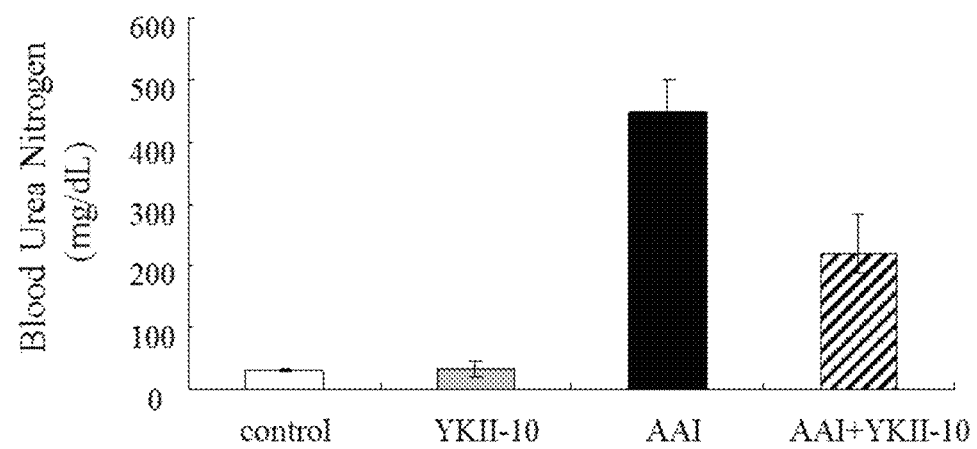
FIG. 4A illustrates the inhibitory effect of the composition YKII-10 of example 1.2 on aristolochic acid (AAI) induced increase in blood urea nitrogen in accordance with one embodiment of the present disclosure.
FIG. 4B illustrates the inhibitory effect of the composition YKII-10 of example 1.2 on aristolochic acid (AAI) induced increase in serum creatinine level in accordance with one embodiment of the present disclosure.
Figure 4:
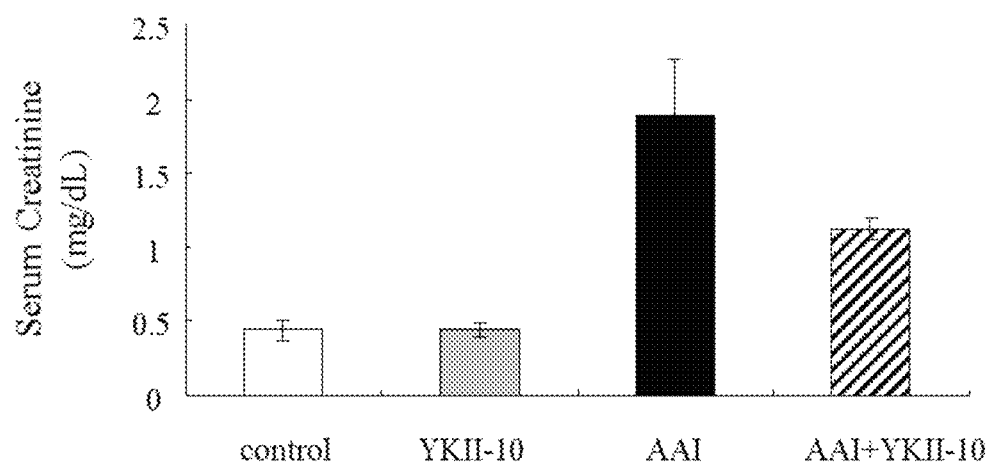

As depicted in FIGS. 4A and 4B, the YKII-10 composition (i.e., the composition of example 1.2) is effective in reducing both the AAI-induced increase in BUN and CRE in the test animals, which support the hypothesis that the composition comprising the compound of formula (I) may be used for the treatment or prophylaxis of kidney disease, including AKI.

4.2 AAI Induced Failure of Glomerular Filtration Rate (GFR)

GFR is the most relevant metric for determining the extent of AKI and progression of chronic kidney disease (CKD). Reduction of GFR secondary to kidney injury, either acute or chronic, are accompanied by increases in blood urine nitrogen (BUN) and serum creatinine (CRE) level. In this example, GFR was measured by monitoring the dissipation of the fluorescence signal of a sugar, i.e., inulin labeled with a fluorescent marker, which can only be metabolized through glomerular filtration.

Blb/c mice (6 weeks old) were randomly assigned to two groups, in which mice in the test group were orally fed with the YKII-10 composition (300 mg/Kg/day) for 8 days, and AAI (2.5 mg/Kg/day) was injected intraperitoneally on the fourth day, and continued the injection for 5 days. By contrast, mice in the control group received only water as their treatment. On the eighth day of the experiment, fluorescent inulin (GFR-Vivo 680, $2 \times 10^{-8}$ mol) was injected into the test animals, and the animals were monitored with a Fluorescence Tomography System (FMT 4000) with images taken at 1, 5, 15, 30 and 45 minutes, respectively. Respective GFR at various time points are calculated and the results are depicted in FIG. 5.

Figure 5:
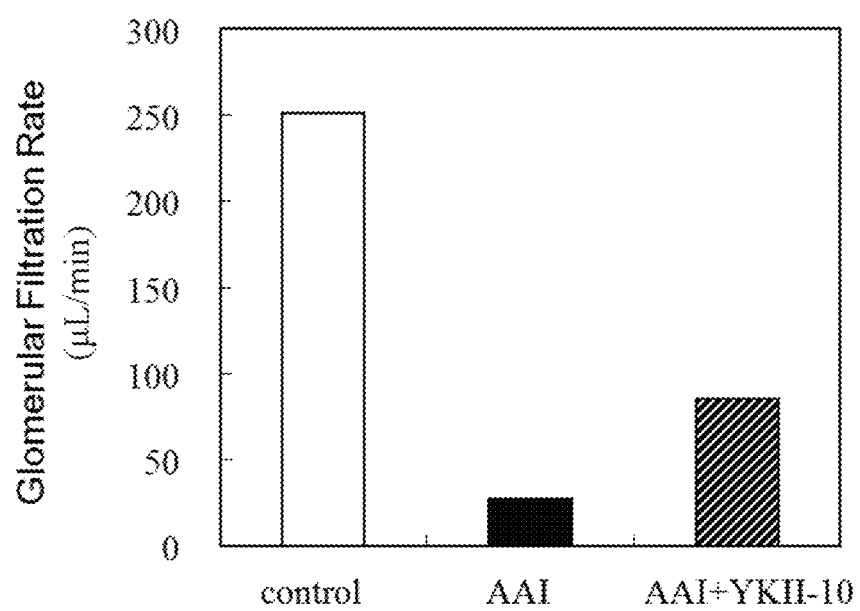
FIG. 5 illustrates the effect of the composition YKII-10 of example 1.2 on glomerular filtration rate (GFR) in accordance with one embodiment of the present disclosure.

As depicted in FIG. 5, AAI treatment knocked down the GFR from its normal value of about 250 μL/min to about 25 μL/min, about 10 folds decreases; however, if the mice were pre-treated with YKII-10 composition of this disclosure, it may have a protective effect on GFR, though GFR value still did not return to its normal value, yet damage to GFR was less significant (about 100 μL/min).

Example 5

YKII-10 Composition of Example 1.2 is Effective in Ameliorating or Improving In Vivo Kidney Function In this example, animals were subjected to surgery to remove part of their kidneys and thereby resulted in a drop in their respective kidney functions to a level that was about ⅙ of a normal value, so as to mimic the kidney function of a subject suffering from chronic kidney disease (CKD). The animals were then treated with the YKII-10 composition of example 1.2 and its effect on enhancing the kidney function was evaluated.

Adult male rats were randomly assigned to two groups (3 rats/group), and ⅔ of the left hand side kidney of each rat in both groups was surgically removed. The animals were left to recover for about a week, then their right hand side kidneys were completely removed by surgery. Such procedure would render the kidney function of the test animal dropped to a level that is about ⅙ of that of a normal animal, thus may mimic the kidney function of a CKD subject. Two weeks after the surgery, animals in the test groups were orally fed with 300 mg/Kg of the YKII-10 composition of example 1.2 on a daily basis, whereas the control animals were merely given water as their treatments. Blood samples were collected every two weeks from the tail of each animals, and estimated GFR (eGFR) of each sample was then calculated by use of the following equation based on blood creatinine level obtained from each sample, and results are illustrated in FIG. 6.

eGFR (mL/min/1.73 m$^2$)=186×(Creatinine level)$^{-1.154}$×(30)$^{-0.203}$

Figure 6:
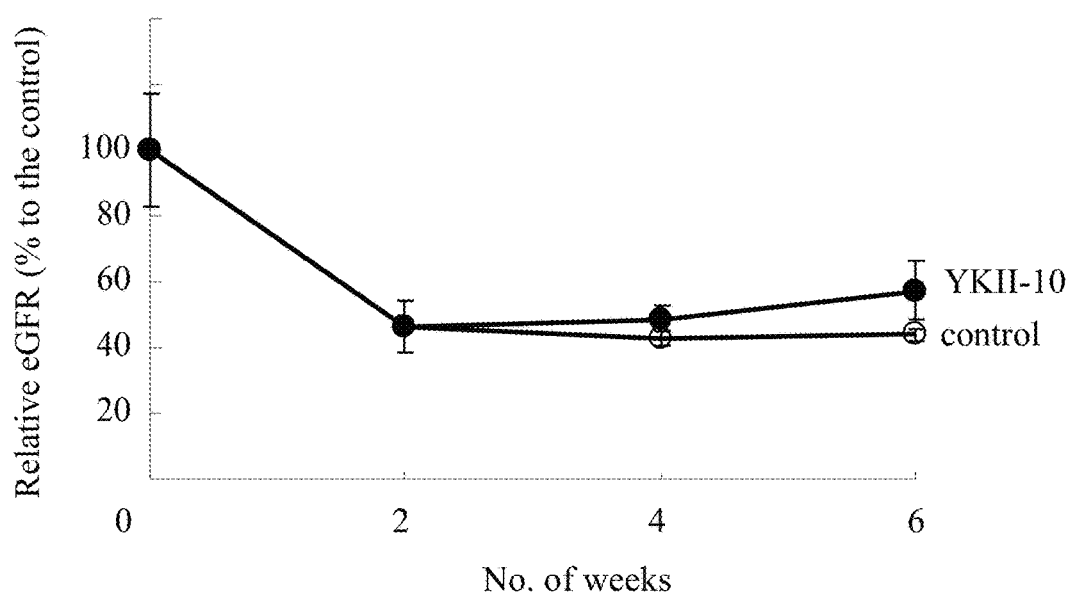
FIG. 6 illustrates the effect of the composition YKII-10 of example 1.2 on relative estimated glomerular filtration rate (eGFR) in accordance with one embodiment of the present disclosure.

As depicted in FIG. 6, eGFR of each rat1 in the test group is about 44% of that of a normal rat. 6 weeks after the surgery, the kidney function of each rats in the test group has slowly gone up to about 59% of that of a normal rat, indicating about 15% increases in the kidney function; whereas the kidney function of each rat in the control group stayed relatively the same, that is, without any sign of improving. Student T-test analysis indicated that the 15% increase in kidney function as illustrated in FIG. 6 is statistically significant, as compared with that of the control.

Taken together, results in this example validate the findings in other examples, and support the hypothesis that the composition comprising the compound of formula (I), may be used for the treatment or prophylaxis of kidney disease, including AKI and CKD.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A method of improving kidney function in a subject having a kidney inflammation or acute kidney injury comprising administering to the subject a compound of formula (I) in a dose of about 1 to 10 mg/Kg, to reduce the levels of blood urine nitrogen (BUN), creatinine (CRE), and urine protein, or to increase the glomerular filtration rate (GFR) of the subject, as compared to those of the subject before administering the compound of formula (I),

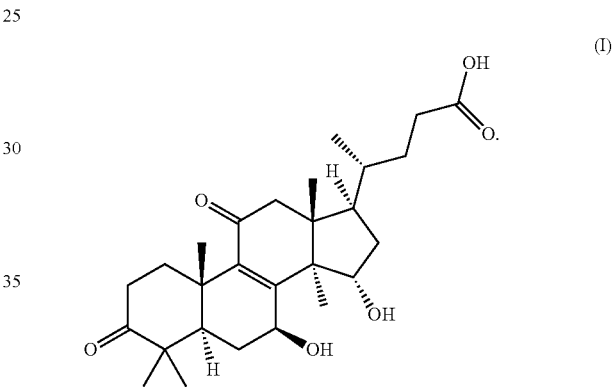

2. The method of claim 1, further comprising administering to the subject an effective amount of lucidenic acid C (LAC), lucidenic acid B (LAB), lucidenic acid N (LAN), lucidenic acid E$_2$ (LAE$_2$), lucidenic acid A (LAA), and lucidenic acid D$_2$ (LAD$_2$).

3. The method of claim 2, wherein the LAC is administered to the subject in a dose of about 1 to 10 mg/Kg.

4. The method of claim 2, wherein the LAA and LAD$_2$ are respectively administered to the subject in a dose of about 2.5 to 25 mg/Kg.

5. The method of claim 2, wherein the LAE$_2$ is administered to the subject in a dose of about 1.5 to 15 mg/Kg.

6. The method of claim 2, wherein the LAN and LAB are respectively administered to the subject in a dose of about 0.85 to 8.5 mg/Kg.

7. The method of claim 1, wherein the subject is a human.

8. The method of claim 1, wherein the subject has acute kidney injury or chronic kidney inflammation.

* * * * *